United States Patent
Nickisch et al.

(10) Patent No.: US 8,222,237 B2
(45) Date of Patent: Jul. 17, 2012

(54) PROGESTATIONAL 3-(6,6-ETHYLENE-17B-HYDROXY-3-OXO-17A-PREGNA-4-ENE-17A-YL)PROPIONIC ACID G-LACTONES

(75) Inventors: Klaus Nickisch, Berlin (DE); Pemmaraju Rao, San Antonio, TX (US); Kesavaram Narkunan, San Antonio, TX (US); James Cessac, Floresville, TX (US)

(73) Assignee: Evestra, Inc., San Antonio, TX (US)

( * ) Notice: Subject to any disclaimer, the term of this patent is extended or adjusted under 35 U.S.C. 154(b) by 428 days.

(21) Appl. No.: 12/626,398

(22) Filed: Nov. 25, 2009

(65) Prior Publication Data

US 2010/0137264 A1 Jun. 3, 2010

Related U.S. Application Data

(60) Provisional application No. 61/117,862, filed on Nov. 25, 2008.

(51) Int. Cl.
*A61K 31/585* (2006.01)
*C07J 19/00* (2006.01)
(52) U.S. Cl. .......................................... 514/173; 540/11
(58) Field of Classification Search .................. 514/173; 540/11
See application file for complete search history.

(56) References Cited

U.S. PATENT DOCUMENTS

| | | |
|---|---|---|
| 3,272,803 A | 9/1966 | Holden |
| 3,510,477 A | 5/1970 | Manson |
| 3,966,713 A | 6/1976 | Hofmeister et al. |
| 4,129,564 A | 12/1978 | Wiechert et al. |
| 4,435,327 A | 3/1984 | Petzoldt |
| 4,501,695 A | 2/1985 | Van Rheenen et al. |
| 4,502,989 A | 3/1985 | Kamata et al. |
| 4,584,288 A | 4/1986 | Nickish et al. |
| 4,868,166 A | 9/1989 | Bittler et al. |
| 5,336,686 A | 8/1994 | Nedelec et al. |
| 5,554,603 A | 9/1996 | Kim et al. |
| 5,981,744 A | 11/1999 | Ng et al. |
| 6,121,465 A | 9/2000 | Mohr et al. |
| 6,933,395 B1 | 8/2005 | Mohr et al. |
| 7,319,154 B2 | 1/2008 | Seilz |
| 2004/0024202 A1 | 2/2004 | Miller et al. |
| 2005/0192450 A1 | 9/2005 | Costantino et al. |
| 2006/0264412 A1 | 11/2006 | Franczyk et al. |
| 2007/0049747 A1 | 3/2007 | Seilz et al. |
| 2008/0076915 A1 | 3/2008 | Cabri et al. |
| 2008/0200668 A1 | 8/2008 | Soros et al. |
| 2008/0207575 A1 | 8/2008 | Costantino et al. |
| 2009/0023914 A1 | 1/2009 | Pontiroli et al. |
| 2009/0029953 A1 | 1/2009 | Bohlmann et al. |
| 2009/0269403 A1 | 10/2009 | Shaked et al. |
| 2010/0130455 A1 | 5/2010 | Nickisch et al. |
| 2010/0273759 A1 | 10/2010 | Nickisch et al. |

FOREIGN PATENT DOCUMENTS

| | | |
|---|---|---|
| DE | 3022337 | 1/1982 |
| HU | 34994 | 5/1985 |

OTHER PUBLICATIONS

International Search Report and Written Opinion for PCT Application No. PCT/US2009/065949, May 24, 2010.
International Preliminary Report on Patentability for PCT Application No. PCT/US2009/065949, May 31, 2011.
Jiang et al. "New progesterone receptor antagonists: Phosphorus-containing 11b-aryl-substituted steroids" Bioorganic & Medicinal Chemistry 14 (2006) 6726-6732.
Teutsch et al. "Synthesis of a Fluorescent Steroid Derivative With High Affinities for the Glucocorticoid and Progesterone Receptors" Steroids (1994), 59, 22-26.
Nickisch et al. "Säure-Katalysierte Umlagerungen Von 15β,16β-Methylen-17a-Pregnen 21,17-Carbolacton-Derivaten" Tetrahedron Letters, vol. 27, No. 45, 5463-5466, 1986.
Giangrande et al. Molecular and Cellular Biology, "The Opposing Transcriptional Activities of the Two Isoforms of the Human Progesterone Receptor Are Due to Differential Cofactor Binding" vol. 20, No. 9, May 2000, p. 3102-3115.
Rao et al. "New 11b-aryl-substituted steroids exhibit both progestational and antiprogestational activity" Steroids 63:523-530, 1998.
Kamata et al. "Aldosterone Antagonists. 2. Synthesis and Biological Activities of 11,12-Dehydropregnane Derivatives" Journal of Medicinal Chemistry, 1987, vol. 30, No. 9, p. 1647-1658.
Nickisch et al. "Aldosterone Antagonists. 1. Synthesis and Activities of 6a,7a:15a,16a-Dimethylene Steroidal Spirolactones" J. Med. Chem. 1985,28, 546-550.
Nickisch et al. "Aldosterone Antagonists. 4. Synthesis and Activities of Steroidal 6,6-Ethylene-15,16-methylene 17-Spirolactones" J. Med. Chem. 1991,34, 2464-2468.
Desai et al. "A Simple High-Yielding Synthesis of Spiro[cyclopropane-1,2'-steroids" Liebigs Ann. Chem., 1990, 711.
Kagawa "Anti-Aldosterones" in Methods in Hormone Research vol. 3 R:I: Dorfmann Academic Press p. 351.
Warwel et al. "Synthese primarer Akylarene ohne Benzol via Olefin-Metathese" Angew. Chem. 94, 1982, 718-719.
Weindel et al. "Interference of C17 Spirosteroids with Late Steps of Aldosterone Biosynthesis Structure-Activity Studies" Arzneimittel Forschung. Drug Research, vol. 41, No. 10, Jan. 1991, p. 1082-1091.
Losert et al. "Progestogens with Antimineralcorticoid Activity" Arzneimittel Forschung. Drug Research, vol. 35, No. 2, 1985, p. 459-471.
International Search Report and Written Opinion for PCT Application No. PCT/US2009/036047, Nov. 9, 2009.
International Preliminary Report on Patentability for PCT Application No. PCT/US2009/036047, Jul. 9, 2010.
Office Action Issued for U.S. Appl. No. 12/397,996 on Jun. 23, 2010.

*Primary Examiner* — Barbara P Badio
(74) *Attorney, Agent, or Firm* — Meyertons, Hood, Kivlin, Kowert & Goetzel, P.C.; Eric B. Meyertons

(57) ABSTRACT

Described herein are 3-(6,6-ethylene-17β-hydroxy-3-oxo-17α-pregna-4-ene-17α-yl)propionic acid γ-lactone derivatives having progestational and aldosterone antagonistic activity. Also described herein are methods of preparing and using these novel compounds.

16 Claims, No Drawings

PROGESTATIONAL 3-(6,6-ETHYLENE-17B-HYDROXY-3-OXO-17A-PREGNA-4-ENE-17A-YL)PROPIONIC ACID G-LACTONES

PRIORITY CLAIM

This application claims priority to U.S. Provisional Patent Application No. 61/117,862, filed on Nov. 25, 2008, entitled "PROGESTATIONAL 3-(6,6-ETHYLENE-17β-HYDROXY-3-OXO-17A-PREGNA-4-ENE-17A-YL)PROPIONIC ACID G-LACTONES" incorporated herein by reference.

BACKGROUND OF THE INVENTION

1. Field of the Invention

The present invention is generally directed to novel 3-(6,6-ethylene-17β-hydroxy-3-oxo-17α-pregna-4-ene-17α-yl) propionic acid γ-lactone derivatives. More particularly, the invention is related to such derivatives having progestational and aldosterone antagonistic activity and methods of preparing and using these compounds.

2. Description of the Relevant Art

Many of the side effects associated with oral contraceptive pills and hormone replacement therapies are due to administration of hormones. Some of the potential side effects from contraceptives and hormone replacement therapies include: depression, vaginal discharge, changes in menstrual flow, breakthrough bleeding, nausea, vomiting, headaches, changes in the breasts, changes in blood pressure, loss of scalp hair, skin problems and skin improvements, increased risk of deep venous thrombosis (DVT) and pulmonary embolism, stroke, increased incidence of cancer, and myocardial infarction (heart attack). The incidence of various side effects appears to be related, to some extent, on the dosage of the progestogen and, in some cases, the estrogen components.

One of the most commonly used combined progestogens is 6β,7β,15β,16β-dimethylene-3-oxo-17α-pregn-4-ene-21,17-carbolactone (drospirenone). This compound is described in German Patent No. 3,022,337. Drospirenone, however, is only sparingly soluble in water at various pH values. The low aqueous solubility of drospirenone reduces its effectiveness due to poor bioavailability. For example, the absolute bioavailability of drospirenone from a single entity tablet is about 76%.

Other methylene-substituted-17α spirolactones have been reported to exhibit the combination of progestational and antialdosterone antagonistic activity. In EP 0 150 157, 6,6-ethylene-15,16-methylene spirolactones are described that exhibit a strong progestational and antialdosterone activity. EP 0 255 464 reports 2,2:6,6-diethylene-3-oxo-17α-pregn-4-ene 21,17-carbolactones having a stronger anti mineralcorticoid activity with a somewhat reduced progestational activity. As described in EP 0 150 157, these compounds are primarily suited for contraceptive use in women with cardiovascular risk factors such as obesity, age, smoking and elevated blood pressure.

Additionally, under acidic conditions (such as encountered in the gastric environment) 17α spirolactones (e.g., drospirenone) undergo isomerization to a form that is inactive. The combination of poor aqueous solubility and potential for isomerization makes the use of low dosage forms of 17α spirolactones difficult. This leads to the use of higher than necessary amounts of 17α spirolactones to counteract the inactivation and slow absorption of the active form.

The use of high dosages of a 17α spirolactones progestogen may lead to an increase in the occurrence of side effects. It is therefore desirable to develop 17α spirolactones progestogens that are highly effective for use in contraceptive and hormone replacement therapies, that are more resistant to the gastric environment, exhibit improved bioavailability, and/or reduce the incidence of side effects.

SUMMARY OF THE INVENTION

In one embodiment, a progestogen compound has the structure of formula (II):

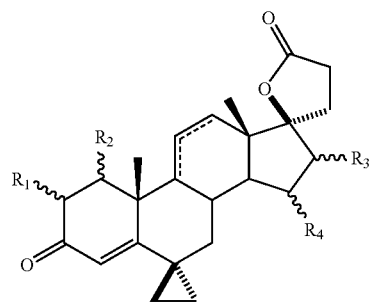

II where the dotted line in Formula II represents a double bond between carbons 9 and 11 or a double bond between carbons 11 and 12;

$R_1$ and $R_2$ are hydrogens, an additional bond between carbons 1 and 2, or a —$CH_2$— bridge between carbons 1 and 2; and $R_3$ and $R_4$ are hydrogens or a —$CH_2$— bridge between carbons 15 and 16.

When the progestogen compound (II) has a double bond between carbons 9 and 11, the progestogen compound has the structure of formula (III):

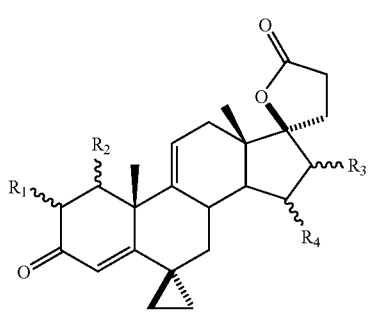

III where $R_1$ and $R_2$ are hydrogens, an additional bond between carbons 1 and 2, or a —$CH_2$— bridge between carbons 1 and 2; and $R_3$ and $R_4$ are hydrogens or a —$CH_2$— bridge between carbons 15 and 16.

When the progestogen compound (II) has a double bond between carbons 11 and 12, the progestogen compound has the structure of formula (IV):

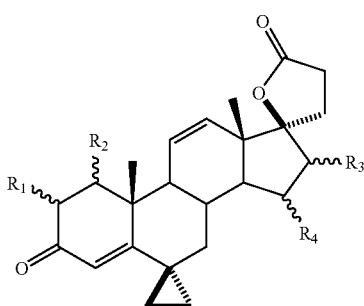

where $R_1$ and $R_2$ are hydrogens, an additional bond between carbons 1 and 2, or a —$CH_2$— bridge between carbons 1 and 2; and $R_3$ and $R_4$ are hydrogens or a —$CH_2$— bridge between carbons 15 and 16.

Compounds of formula (II) may be used to produce a contraceptive state in a subject when an oral dosage form comprising an effective amount of a progestogen compound (II) is administered to the subject.

In another embodiment, a progestogen compound has the structure of formula (V):

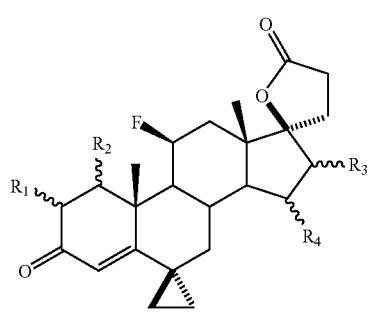

where $R_1$ and $R_2$ are hydrogens, an additional bond between carbons 1 and 2, or a —$CH_2$— bridge between carbons 1 and 2; and $R_3$ and $R_4$ are hydrogens or a —$CH_2$— bridge between carbons 15 and 16.

Compounds of formula (V) may be used to produce a contraceptive state in a subject when an oral dosage foam comprising an effective amount of a progestogen compound (V) is administered to the subject.

DETAILED DESCRIPTION OF THE PREFERRED EMBODIMENTS

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

Unless defined otherwise, all technical and scientific terms used herein have the same meaning as commonly understood by one of ordinary skill in the art.

Compounds described herein embrace both racemic and optically active compounds. Chemical structures depicted herein that do not designate specific stereochemistry are intended to embrace all possible stereochemistries.

It will be appreciated by those skilled in the art that compounds having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound. As used herein, the term "single stereoisomer" refers to a compound having one or more chiral center that, while it can exist as two or more stereoisomers, is isolated in greater than about 95% excess of one of the possible stereoisomers. As used herein a compound that has one or more chiral centers is considered to be "optically active" when isolated or used as a single stereoisomer.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

Described herein are progestogen compounds, methods of making progestogen compounds and methods of using progestogen compounds. Progestogen are hormones that produce effects similar to those of progesterone. Progestogens have antiestrogenic (counteracting the effects of estrogens on the body) and antigonadotropic (inhibiting the production of sex steroids by gonads) properties. For the structures described herein, the standard steroid numbering scheme is used. Specifically, steroids are numbered according to the general formula (I) below.

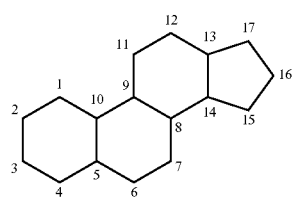

In one embodiment, a progestogen compound has the structure of formula (II):

where the dotted line in Formula II represents a double bond between carbons 9 and 11 or a double bond between carbons 11 and 12;

$R_1$ and $R_2$ are hydrogens, an additional bond between carbons 1 and 2, or a —$CH_2$— bridge between carbons 1 and 2; and $R_3$ and $R_4$ are hydrogens or a —$CH_2$— bridge between carbons 15 and 16.

In an embodiment, when the progestogen compound has a double bond between carbons 9 and 11, the progestogen compound has the structure of formula (III):

Specific examples include:

IIIa:

$R_1, R_2 = H$
$R_3, R_4 = H$

IIIb:

$R_1, R_2 = H$
$R_3, R_4 = CH_2$ bridge

IIIc:

$R_1, R_2 =$ double bond
$R_3, R_4 = H$

IIId:

$R_1, R_2 =$ double bond
$R_3, R_4 = CH_2$ bridge

IIIe:

$R_1, R_2 = CH_2$ bridge
$R_3, R_4 = H$

IIIf:
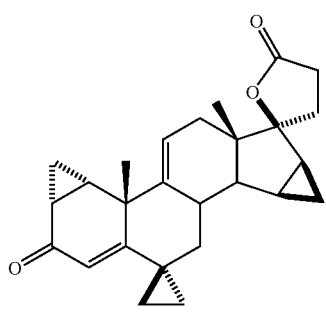
R₁, R₂ = CH₂ bridge
R₃, R₄ = CH₂ bridge
In an embodiment, when the progestogen compound has a double bond between carbons 11 and 12, the progestogen compound has the structure of formula (IV):
IV
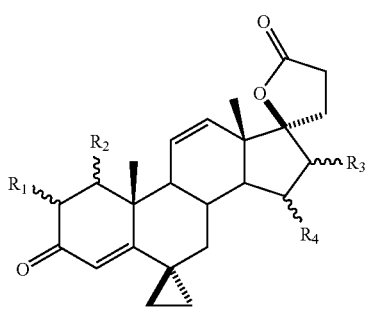
Specific examples include:
IVa:
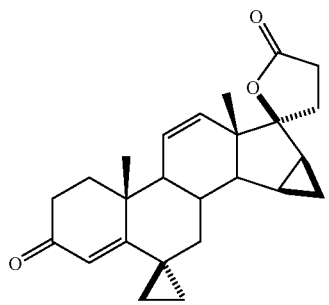
R₁, R₂ = H
R₃, R₄ = H
IVb:
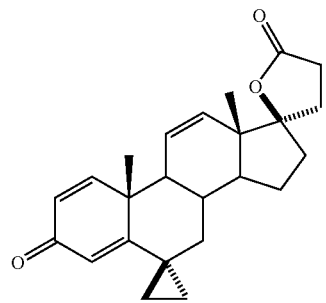
R₁, R₂ = H
R₃, R₄ = CH₂ bridge
IVc:
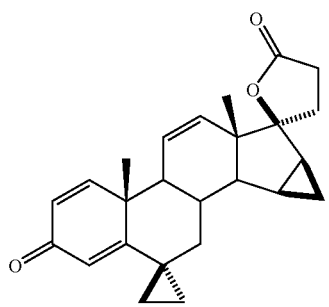
R₁, R₂ = double bond
R₃, R₄ = H
IVd:
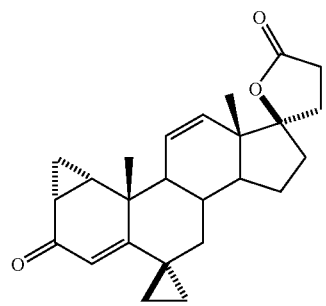
R₁, R₂ = double bond
R₃, R₄ = CH₂ bridge
IVe:
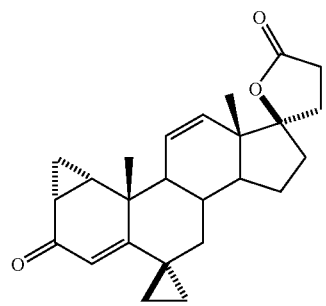
R₁, R₂ = CH₂ bridge
R₃, R₄ = H IVf:

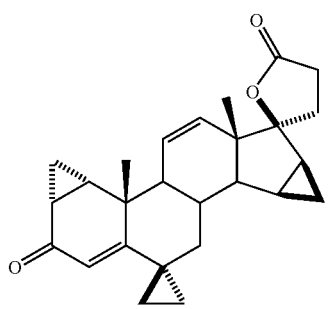

R₁, R₂ = CH₂ bridge
R₃, R₄ = CH₂ bridge

In another embodiment, a progestogen compound has the structure of formula (V):

V

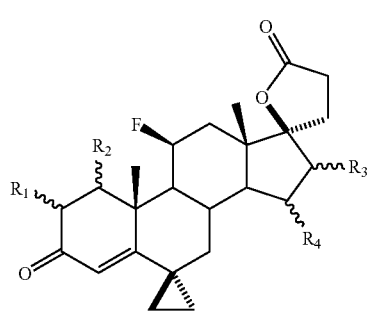

$R_1$ and $R_2$ are hydrogens, an additional bond between carbons 1 and 2, or a —CH₂— bridge between carbons 1 and 2; and $R_3$ and $R_4$ are hydrogens or a —CH₂— bridge between carbons 15 and 16.

Specific examples include:

Va:

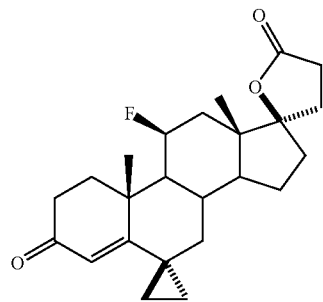

R₁, R₂ = H
R₃, R₄ = H

Vb:

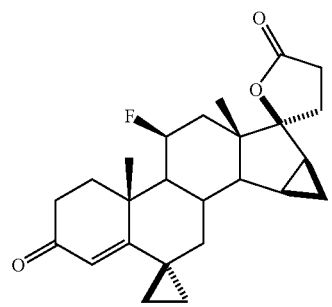

R₁, R₂ = H
R₃, R₄ = CH₂ bridge

Vc:

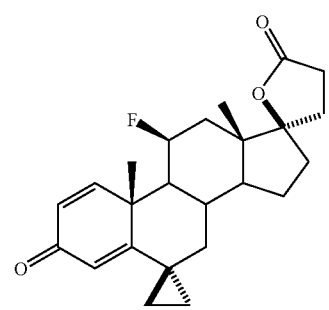

R₁, R₂ = double bond
R₃, R₄ = H

Vd:

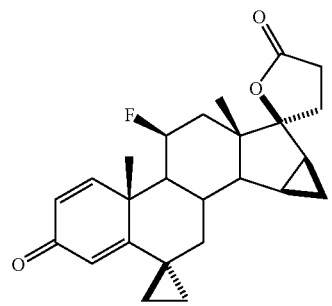

R₁, R₂ = double bond
R₃, R₄ = CH₂ bridge

Ve:

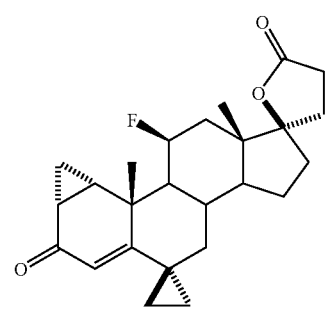

R₁, R₂ = CH₂ bridge
R₃, R₄ = H

Vf:

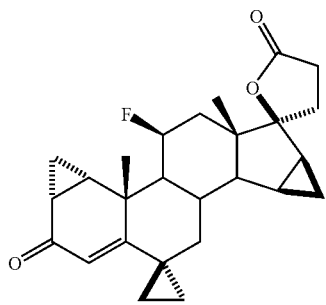

R₁, R₂ = CH₂ bridge
R₃, R₄ = CH₂ bridge

The above described progestogen compounds show a more balanced endocrinological profile, making them ideal candidates for broad application as contraceptives.

The doses of the progestogen compounds described herein in oral contraceptive products are preferentially between 0.3 and 5.0 mg per day. The progestogen compounds may be administered in combination with an estrogen. In some embodiments, the progestogen compounds may be combined with ethinylestradiol. When combined with ethinylestradiol, the amount of ethinylestradiol used is in the range of 0.2 to 0.35 mg per day.

The following biological tests were used to characterize the biological activity of the progestogen derivatives.

Progestin receptor binding assay: This assay involves competitive binding to recombinant human progesterone receptors A and B using [$^3$H]progesterone as the standard. The IC$_{50}$ and relative binding affinity (RBA) were tested in two independent assays at 7-8 concentrations.

Androgen receptor binding assay: This assay involves competitive binding to recombinant rat androgen receptor ligand binding domain (ARLBD) using [$^3$H]R1881 as the standard. The IC$_{50}$ and relative binding affinity (RBA) were tested in two independent assays at 7-8 concentrations.

Mineralocorticoid activity was tested according to the method of Kagawa (1964) Anti-aldosterones, in Methods in Hormone Research vol. 3 R:I: Dorfmann Academic Press p. 351

Androgen transactivation assay: This assay involves transient transfection of a luciferase reporter vector containing three progestin/glucocorticoid/androgen response elements (3XHRE-LUC) and a human androgen receptor expression vector (pCMV5hAR3.1) into CV-1 African green monkey kidney cells and treating the transfected cells with the test compound at 10-13 different concentrations to obtain a dose-response curve and estimate an EC$_{50}$. To test for antagonist activity, various concentrations of the test compound were used to block testosterone-induced transactivation of 3XHRE-LUC.

Synthesis of various derivatives of compounds having the formula (II), where R₁, R₂=H, may be prepared as indicated in Scheme 1, from the corresponding compounds (VI). Examples of this procedure may be found, for example, in the paper to Nickischet al. "Aldosterone Antagonists. 4. Synthesis and Activities of Steroidal 6,6-Ethylene 17-Spirolactones." J. Med. Chem., 34, 2464-2468 (1991), which is incorporated herein by reference.

Scheme 1

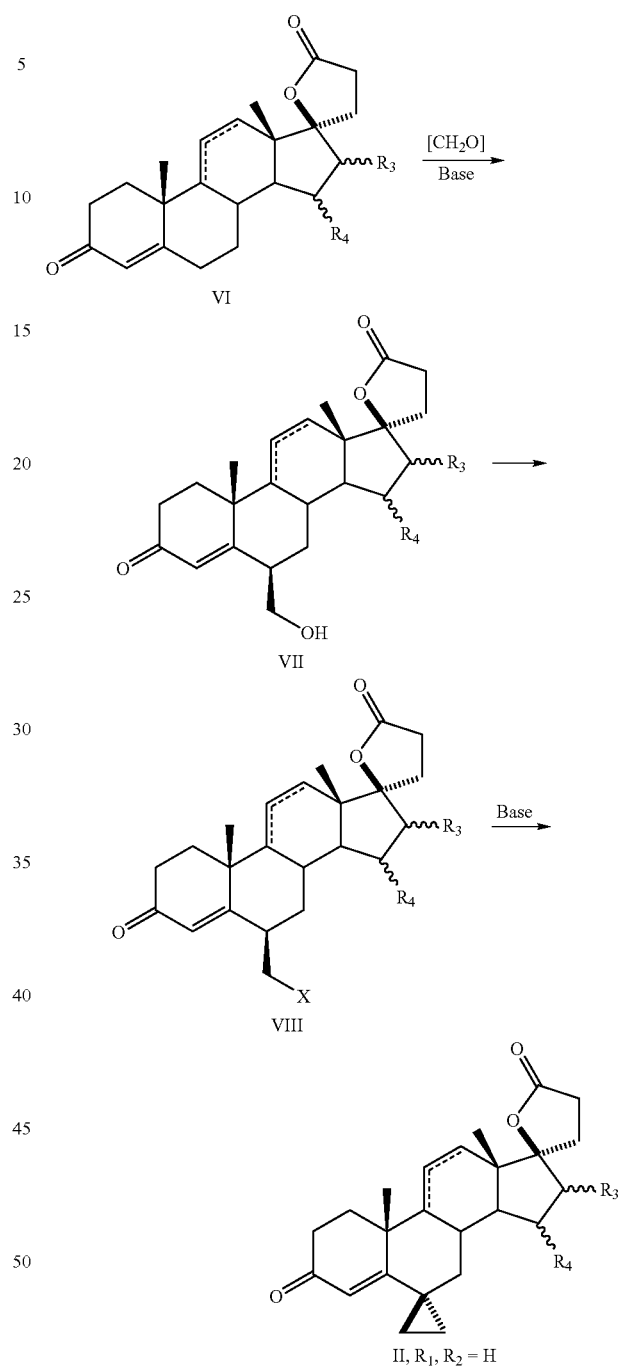

Reaction of compounds of general structure (VI) with a base in the presence of formaldehyde or a formaldehyde equivalent (for example, formalin, halomethyl alkyl ethers, dialkoxymethanes (such as dimethoxymethane or diethoxymethane), etc.) yields the desired 6-hydroxymethyl compounds of general formula (VII). Reaction of the hydroxymethyl compounds of general formula (VII) with an appropriate reactant will functionalize the hydroxy group to form a leaving group "X" as depicted in formula (VIII). Examples of leaving groups include, but are not limited to I, Cl, Br, tosyl, brosyl, mesyl, or trifyl. Finally, treatment of the compounds of general formula (VIII) with a methylene ylid gives the target compounds of general formula (II, $R_1$, $R_2$=H). Phosphorous or sulfur ylids may be used. In one embodiment, a sulfur ylid formed by the reaction of trimethylsulfoxonium iodide and a strong base (e.g., NaH) in an aprotic solvent (e.g., dimethylsulfoxide)) may be used.

Compounds of general formula (II) wherein $R_1$ and $R_2$ represent a double bond between carbons 1 and 2 may be prepared as shown below in Scheme 2.

Scheme 2

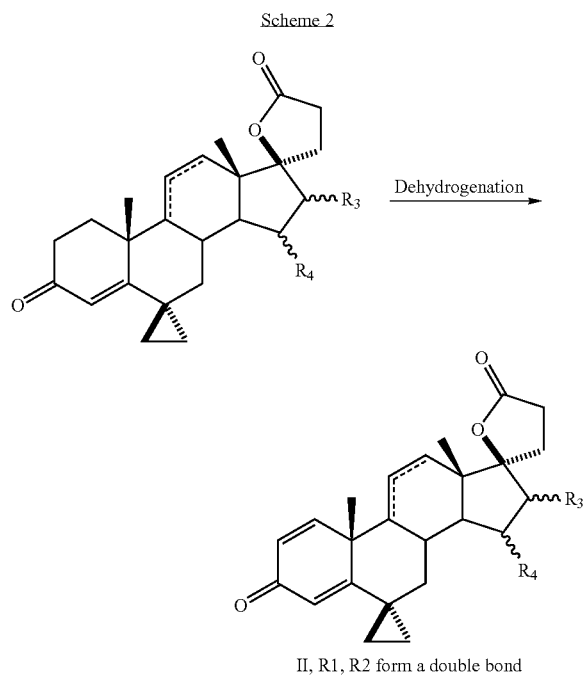

II, R1, R2 form a double bond

Reaction of compounds of general structure (II, $R_1$, $R_2$ are hydrogen) with a suitable dehydrogenating agent gives the corresponding $\Delta^{1,4,9(11)}$-3-one derivatives of general formula (II, $R_1$, $R_2$ for a double bond). Examples of suitable dehydrogenating agents include, but are not limited to, metals (e.g., Pd, Pt, etc.), sulfur, selenium, and quinones (e.g., dichlorodicyanoquinone, tetrachloroquinone, etc.).

Compounds of general formula (II) wherein $R_1$ and $R_2$ represent a $CH_2$ bridging group may be prepared as indicated below in Scheme 3. Examples of this procedure may be found, for example, in the paper to Nickisch et al. "Aldosterone Antagonists. 1. Synthesis and Activities of 6β,7β:15β,16β-Dimethylene Steroidal Spirolactones." J. Med. Chem. 28, 546-550 (1985), which is incorporated herein by reference.

Scheme 3

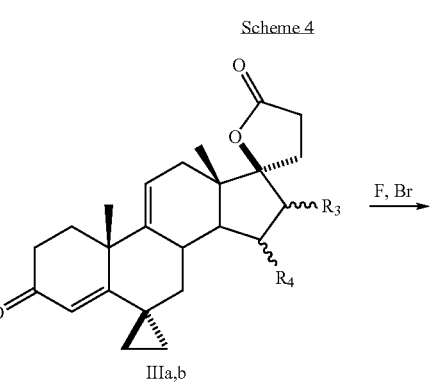

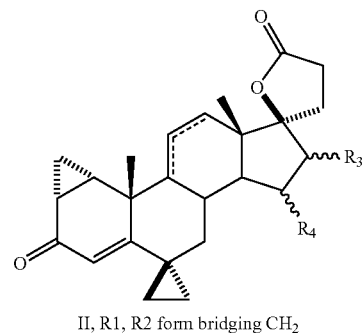

II, R1, R2 form bridging CH2

Reaction of compounds of general formula (II, $R_1$, $R_2$ form a double bond) with a methylene ylid gives the target compounds of general formula (II, $R_1$, $R_2$ are a bridging $CH_2$). Phosphorous or sulfur ylids may be used. In one embodiment, a sulfur ylid formed by the reaction of trimethylsulfoxonium iodide and a strong base (e.g., NaH) in an aprotic solvent (e.g., dimethylsulfoxide)) may be used.

Compounds of general formula (V) wherein $R_1$, $R_2$=H can be prepared from compounds of general formula (IIIa,b) as shown below in Scheme 4. Examples of this procedure may be found, for example, in U.S. Pat. No. 3,966,713, which is incorporated herein by reference.

Scheme 4

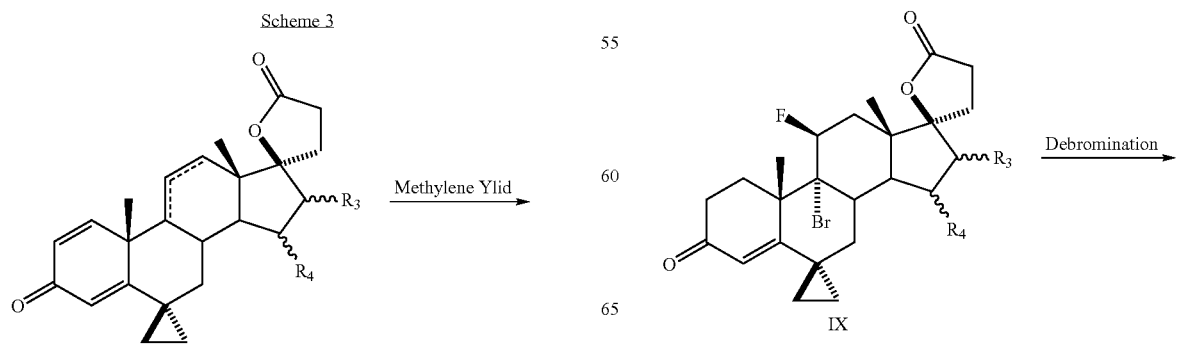

-continued

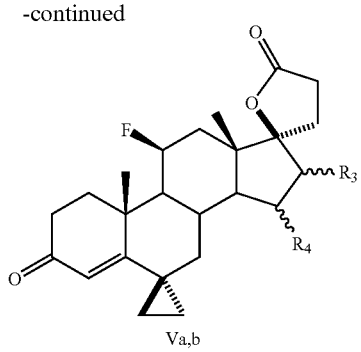

Va,b

Reaction of compounds of general formula (IA) with fluorine and bromine gives the 11-fluoro, 9-bromo derivative of general formula (IX). In one embodiment, formation of the derivative (IX) (may be accomplished with hydrogen fluoride and N-bromosuccinimide in dimethylformamide at a temperature of −78 to −30° C. Debromination of compounds of general formula (IX) using a suitable agent (e.g., trialkyltin hydride in the presence of a radical-forming agent (e.g., α,α-azodiisobutyronitrile)) gives the corresponding 11β-fluoro derivatives of general formula (Va,b).

Compounds of general formula (Vc,d) may be prepared from compounds of general formula (Va,b), respectively, as shown below in Scheme 5.

Scheme 5

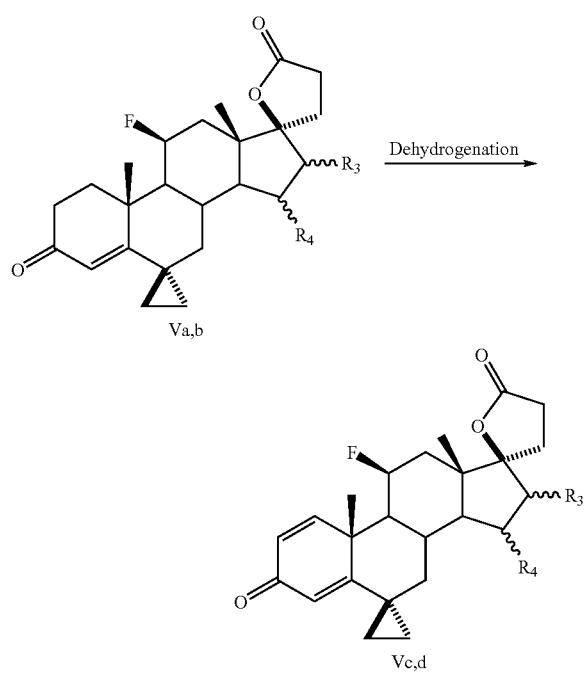

Reaction of compounds of general structure (Va,b) with a suitable dehydrogenating agent gives the corresponding $\Delta^{1,4}$-3-one derivatives of general formula (Vc,d). Examples of suitable dehydrogenating agents include, but are not limited to, metals (e.g., Pd, Pt, etc.), sulfur, selenium, and quinones (e.g., dichlorodicyanoquinone, tetrachloroquinone, etc.).

Compounds of general formula (Ve,f) may be prepared as indicated below in Scheme 6. Examples of this procedure may be found, for example, in the paper to Nickisch et al. "Aldosterone Antagonists. 1. Synthesis and Activities of 6β,7β:15β,16β-Dimethylene Steroidal Spirolactones" J. Med. Chem. 28, 546-550 (1985), which is incorporated herein by reference.

Scheme 6

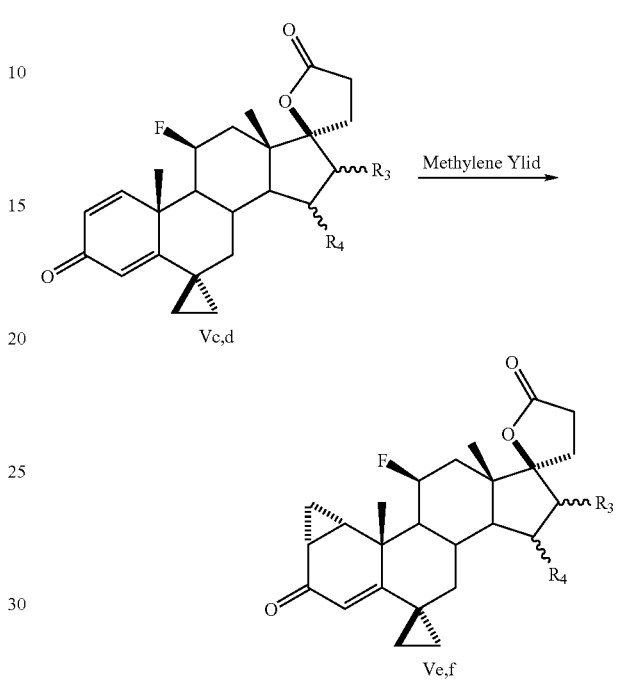

Reaction of compounds of general formula (Vc,d) with a methylene ylid gives the target compounds of general formula (Ve,f). Phosphorous or sulfur ylids may be used. In one embodiment, a sulfur ylid formed by the reaction of trimethylsulfoxonium iodide and a strong base (e.g., NaH) in an aprotic solvent (e.g., dimethylsulfoxide)) may be used.

In one embodiment, the progestogen compounds disclosed herein may be used to produce a contraceptive state in a subject. The method of achieving such a state includes administering, to said subject, on each day of at least 21 consecutive days, a progestogen compound described herein. The method further includes administering, on each day of 7 or less consecutive days, a daily dosage unit containing no active agent, or alternatively, administering no dosage units for 7 days or less.

In suitable embodiments of this method, the daily dosage units including a combination a progestogen compound described herein may be administered for 21, 22, 23 or 24 consecutive days, and the daily dosage units containing no active agent may then be administered for 7, 6, 5 or 4 consecutive days, as appropriate. Furthermore, the daily dosage units including the progestogen compounds described herein may be administered for 28 consecutive days.

Alternatively, the present method includes administering, on each day of at least 21 consecutive days, a daily dosage unit that includes a progestogen compound as described herein, followed by administering, on each day of 7 or less consecutive days, a daily dosage unit containing an estrogen alone in an amount of from about 0.01 mg to about 1.0 mg. Oral dosage forms of an estrogen may be formed by hot-melt extrusion, as described above or any of known tableting procedures.

In this alternative method, the daily dosage units that include a progestogen compound as described herein may suitably be administered for 21, 22, 23 or 24 consecutive days, and the daily dosage units that include an estrogen alone may then be administered for 7, 6, 5 or 4 consecutive days, as appropriate.

Further embodiments described herein also relate to oral dosage forms that are designed to inhibit ovulation in a human female by the administration of a combination of a progestogen compound disclosed herein and an estrogen.

Estrogens include, but are not limited to, estradiol (17β-estradiol), estridiol acetate, estradiol benzoate, estridiol cypionate, estridiol decanoate, estradiol diacetate, estradiol heptanoate, estradiol valerate, 17α-estradiol, estriol, estriol succinate, estrone, estrone acetate, estrone sulfate, estropipate (piperazine estrone sulfate), ethynylestradiol (17α-ethynylestradiol, ethinylestradiol, ethinyl estradiol, ethynyl estradiol), ethynylestradiol 3-acetate, ethynylestradiol 3-benzoate, mestranol, quinestrol, and nitrated estrogen derivatives.

Nitrated estrogen derivatives are described in U.S. Pat. No. 5,554,603 to Kim et al. which is incorporated herein by reference. Nitrated estrogen derivatives that may be used in combination with a progestogen include compounds having the structure:

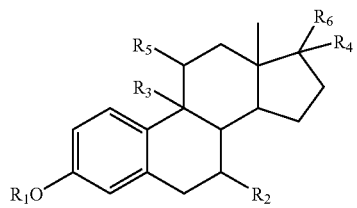

where $R_1$ is hydrogen, $C_1$-$C_8$ alkyl, cycloalkyl, or $C_1$-$C_8$ acyl;
$R_2$ is hydrogen or $C_1$-$C_8$ alkyl;
$R_3$ is hydrogen, hydroxy or $C_1$-$C_8$ alkyl;
$R_4$ is hydrogen or $C_1$-$C_8$ alkyl;
where each $R_5$ and $R_6$ is, independently, hydrogen or nitrate; and wherein at least one of $R_5$ and $R_6$ is a nitrate group.

In some embodiments, the nitrated estrogen derivative has the structure:

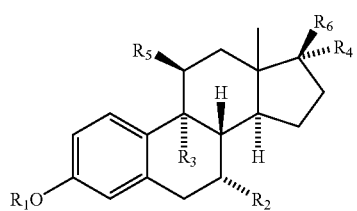

where $R_1$ is hydrogen, $C_1$-$C_8$ alkyl, cycloalkyl, or $C_1$-$C_8$ acyl;
$R_2$ is hydrogen or $C_1$-$C_8$ alkyl;
$R_3$ is hydrogen, hydroxy or $C_1$-$C_8$ alkyl;
$R_4$ is hydrogen or $C_1$-$C_8$ alkyl;
where each $R_5$ and $R_6$ is, independently, hydrogen or nitrate;
and wherein at least one of $R_5$ and $R_6$ is a nitrate group.

A specific compound that may be used in combination with a progestogen in an oral contraceptive to inhibit ovulation in a female subject includes the compound (+)-3,11β,17β-trihydroxyestra-1,3,5(10)-triene 11,17-dinitrate ester, which has the structure:

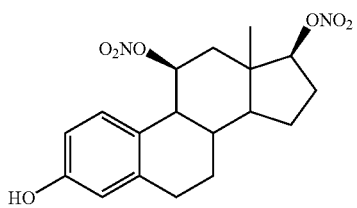

In one embodiment, a combination of a progestogen compound disclosed herein and an estrogen compound may be used to produce a contraceptive state in a subject. The method of achieving such a state includes administering, to said subject, on each day of at least 21 consecutive days, a daily oral dosage unit, that includes a combination of the progestogen and the estrogen. The method further includes administering, on each day of 7 or less consecutive days, a daily dosage unit containing no active agent, or alternatively, administering no dosage units for 7 days or less.

In suitable embodiments of this method, the combination of a progestogen compound disclosed herein and an estrogen compound may be administered for 21, 22, 23 or 24 consecutive days, and a daily dosage units containing no active agent may then be administered for 7, 6, 5 or 4 consecutive days, as appropriate. Furthermore, the combination of a progestogen compound disclosed herein and an estrogen compound may be administered for 28 consecutive days.

Specific oral dosage forms described herein for use as an oral contraceptive include one or more progestogen compounds disclosed herein and the estrogen compound ethinylestradiol in amounts effective to inhibit ovulation in a female subject. An oral dosage form may include, but is not limited to, between about 0.5 mg to about 50 mg, between about 1 mg to 30 mg, or between about 2 mg to 10 mg of progestogen compounds disclosed herein. An oral dosage form includes, but is not limited to, 1 mg, 1.5 mg, 2 mg, 2.5 mg, 3 mg, 3.5 mg, 4 mg, 4.5 mg, or 5 mg of progestogen compounds disclosed herein.

In addition to a progestogen compound disclosed herein, an oral dosage form further includes ethinylestradiol. An oral dosage form may include, but is not limited to, between about 0.01 mg to about 0.05 mg, between about 0.015 mg to 0.04 mg, or between about 0.02 mg to 0.03 mg of ethinylestradiol. An oral dosage form includes, but is not limited to, 0.01 mg, 0.015 mg, 0.02 mg, 0.025 mg, 0.03 mg, 0.035 mg, 0.04 mg, 0.045 mg, or 0.05 mg of ethinylestradiol.

Another specific oral dosage form includes a combination of one or more progestogen compounds disclosed herein and a nitrated estrogen derivative. The oral dosage form may include, but is not limited to, between about 0.5 mg to about 50 mg, between about 1 mg to 30 mg, or between about 2 mg to 10 mg of one or more progestogen compounds disclosed herein. An oral dosage form includes, but is not limited to, 1 mg, 1.5 mg, 2 mg, 2.5 mg, 3 mg, 3.5 mg, 4 mg, 4.5 mg, or 5 mg of one or more progestogen compounds disclosed herein.

In addition to one or more progestogen compounds disclosed herein, an oral dosage form further includes a nitrated estrogen derivative. The oral dosage form may include, but is not limited to, between about 0.01 mg to about 1.0 mg of a nitrated estrogen derivative. An oral dosage form includes, but is not limited to, 0.01 mg, 0.05 mg, 0.1 mg, 0.2 mg, 0.3 mg, 0.4 mg, 0.5 mg, 0.7 mg, or 1.0 mg of a nitrated estrogen derivative.

Oral dosage forms may be made using any known techniques. In one embodiment, oral dosage forms may be made by a tableting process in which the progestogen compound, and optionally, the estrogen compound are disposed in a compressed tablet. When in the form of a tablet, the progestogen compound may be in micronized form (i.e., having a particle size of less than 100 μm).

In an alternate embodiment, oral dosage forms may include a progestogen dispersed in an enteric polymer and, optionally an estrogen. Such oral dosage forms may be prepared by the process described in U.S. Patent Publication No. 2009/0269403, which is incorporated herein by reference, using the progestogen compounds described herein in place of drospirenone.

While oral dosage forms may be a preferred embodiment of delivery, it should be understood that any suitable route of administration may be employed for providing a patient with an effective dosage of progestogen compounds described herein. For example, rectal, topical, parenteral, ocular, pulmonary, nasal, and the like may be employed. Dosage forms include tablets, troches, dispersions, suspensions, solutions, capsules, creams, ointments, aerosols, and the like.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

6β-(Hydroxymethyl)-15β-16β-methylene-3-oxo-17α-pregna-4,9(11)-diene-21,17-carbolactone (VIIa)

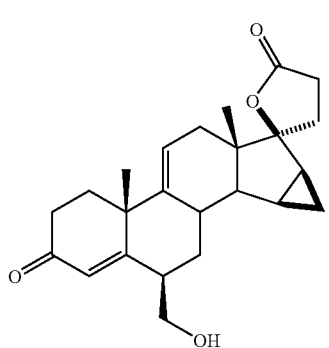

VIIa

A solution of 15β,16β-Methylene-3-oxo-17α-pregna-4,9(11)-diene-21,17-carbolactone (4.0 g, 11.35 mmol) in 35 mL methanol was combined with pyrrolidine (2 mL, 24 mmol) and heated for 20 min under reflux. After cooling, the precipitated 3-pyrrolidinyl intermediate was suctioned off and washed with a small amount of cold methanol and dried. This material was dissolved in 45 mL benzene and 90 mL ethanol and treated dropwise with formalin solution (37%, 4.5 mL, ~30 mmol). The mixture was stirred for 1 hr at room temperature and concentrated under vacuum. The resultant crude mixture was purified by chromatography followed by crystallization to give the pure 6β-hydroxymethyl derivative (VIIa, 1.95 g, 45%). IR (ATR) $v_{max}$ 3410, 1765, 1670, 1650, 1615 cm$^{-1}$. NMR (300 mHz, CDCl$_3$) δ 0.85 (s, CH$_3$), 0.95 (s, CH$_3$), 3.75 (m, CH$_2$OH), 5.6 (m, C11-H), 5.8 (m, C4-H).

EXAMPLE 2

6,6-Ethylene-15β,16β-methylene-3-oxo-17α-pregna-4,9(11)-diene-21,17-carbolactone (IIIb)

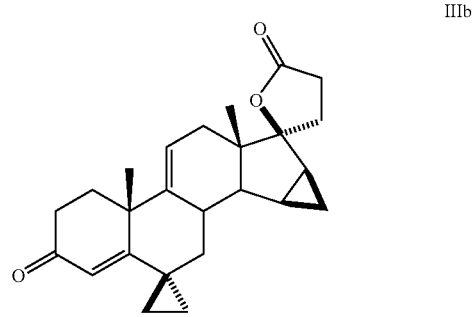

IIIb

A solution of the compound of Example 1 (VIIa, 1.9 g, 5 mmol) in pyridine (20 mL) was combined with p-toluenesulfonyl chloride (2.86 g, 15 mmol). The mixture was stirred for 3 h at room temperature, combined with 0.3 mL water, and stirred for another hour. The crude product was precipitated into ice water, filtered off, washed with water and dried. A solution of trimethylsulfoxonium iodide (3.84 g, 17.4 mmol) in DMSO (75 mL) was combined with sodium hydride (60% oil suspension, 0.57 g, 14.2 mmol) and stirred for 1 h at room temperature. To this solution was added the dried crude tosylate dissolved in DMSO (2 mL) dropwise. The reaction mixture was stirred for 30 min and precipitated into ice water. The crude product was collected by filtration, washed with water, dried and purified by chromatography to give the pure 6,6-ethylene compound (IIIb, 0.8 g, 42%). IR (ATR) $v_{max}$ 1765, 1670, 1650, 1615 cm$^{-1}$. NMR (300 mHz, CDCl$_3$) δ 0.85 (s, CH$_3$), 0.95 (s, CH$_3$), 5.6 (m, C11-H), 5.8 (m, C4-H).

EXAMPLE 3

6,6-Ethylene-15β,16β-methylene-3-oxo-17α-pregna-1,4,9(11)-triene-21,17-carbolactone (IIId)

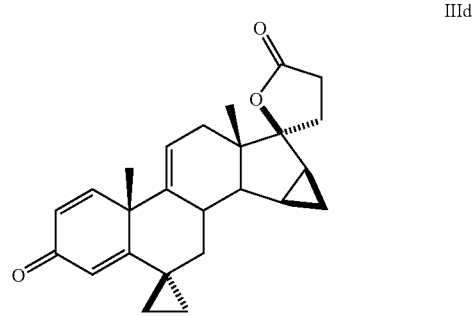

IIId

A solution of the compound of Example 3 (IIIb, 3.2 g, 8.5 mmol) and 2,3-dichloro-5,6-dicyano-p-benzoquinone (DDQ, 3.5 g, 15.4 mmol) in toluene (50 mL) was heated for 5 h at 100° C. The reaction solution was then diluted with ether, washed with sodium bicarbonate solution and water, dried over Na$_2$SO$_4$, and evaporated. The residue was purified by chromatography followed by crystallization to give the pure 1,4,9(11)-triene derivative (IIId, 2.1 g, 67%). IR (ATR) ν$_{max}$ 1770, 1660, 1630, 1620 cm$^{-1}$. NMR (300 mHz, CDCl$_3$) δ 1.09 (s, CH$_3$), 1.22 (s, CH$_3$), 5.6 (m, C11-H), 6.13 (d, C4-H), 6.3 (dd, C2), 7.2 (d, C1) ppm.

EXAMPLE 4

1α,2α:15β16β-Dimethylene-6,6-ethylene-3-oxo-17α-pregna-4,9(11)-diene-21,17-carbolactone (IIIf)

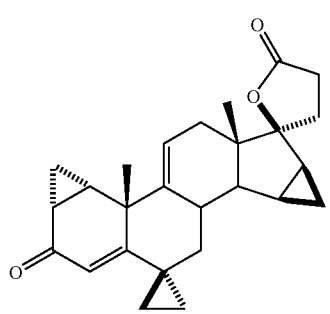

IIIf

A solution of trimethylsulfoxonium iodide (1.75 g, 8 mmol) in DMSO (20 mL) was added to sodium hydride (60% oil suspension; 0.175 g, 7.25 mmol) and stirred for 1 h at room temperature. To this solution was added the 1,4,9(11)-triene derivative (IIId, 1.6 g, 4.25 mmol) dissolved in DMSO (5 mL) dropwise. The reaction mixture was then stirred at room temperature until the reaction was complete as evidenced by tlc. The reaction mixture was poured into ice water and neutralized with sulfuric acid. The resulting precipitate was collected by filtration, washed with water and dried. The crude product was purified by chromatography followed by crystallization to give the pure 1α,2α-methylene derivative (IIIf, 0.5 g, 30%) as a foam. IR (ATR) ν$_{max}$ 1770, 1660, 1630, 1620 cm$^{-1}$. NMR (300 mHz, CDCl$_3$) δ 1.05 (s, CH$_3$), 1.35 (s, CH$_3$), 5.6 (m, C11-H), 5.8 (s, C4-H) ppm.

EXAMPLE 5

6β-(Hydroxymethyl)-15β,16β-methylene-3-oxo-17α-pregna-4,11-diene-21,17-carbolactone (IVb)

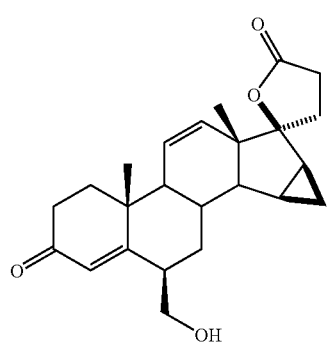

VIIb

As described in Example 1, 15β,16β-Methylene-3-oxo-17α-pregna-4,11-diene-21,17-carbolactone (4.0 g, 11.35 mmol) was reacted with pyrrolidine (2 mL) in methanol (35 mL) at reflux. The thus formed 3-pyrrolidinyl intermediate was then reacted with 5 mL 37% formalin in 45 mL benzene and 90 mL ethanol to give the crude product. Purification by chromatography followed by crystallization gave the pure 6β-hydroxymethyl derivative (VIIb, 2.1 g, 48%). IR (ATR) ν$_{max}$ 3412, 1765, 1675, 1650, 1615 cm$^{-1}$. NMR (300 mHz, CDCl$_3$) δ 0.85 (s, CH$_3$), 0.95 (s, CH$_3$), 3.75 (m, CH$_2$OH), 5.6-5.8 (m, C11-H and C12-H), 5.95 (s, C4-H).

EXAMPLE 6

6,6-Ethylene-15β,16β-methylene-3-oxo-17α-pregna-4,11-diene-21,17-carbolactone (IVb)

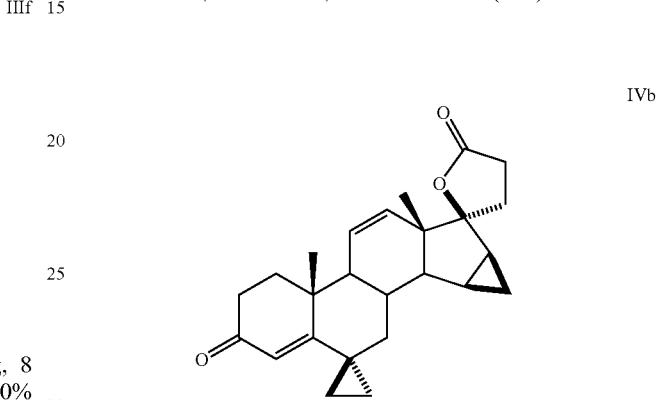

IVb

As described in Example 2, a solution of the compound of Example 5 (VIIb, 2.0 g, 5.3 mmol) in pyridine (20 mL) was reacted with p-toluenesulfonyl chloride (2.86 g, 15 mmol) followed by reaction of the crude tosylate thus formed with trimethysulfoxonium iodide (3.84 g, 17.4 mmol) and sodium hydride (60% oil suspension, 0.57 g, 14.2 mmol) to give the crude product. Purification by chromatography gave the pure 6,6-ethylene compound (IVb, 0.9 g, 45%). IR (ATR) ν$_{max}$ 1765, 1670, 1650, 1615 cm$^{-1}$. NMR (300 mHz, CDCl$_3$) δ 0.85 (s, CH$_3$), 0.95 (s, CH$_3$), 5.6-5.8 (m, C11-H and C-12H), 6.1 (m, C4-H).

EXAMPLE 7

6,6-Ethylene-15β,16β-methylene-3-oxo-17α-pregna-1,4,11-triene-21,17-carbolactone (IVd)

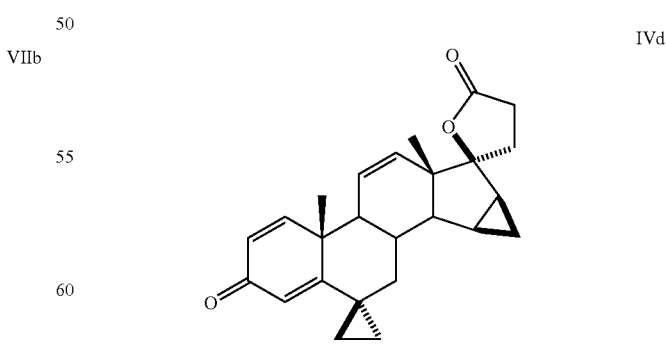

IVd

As described in Example 3, a solution of the compound of Example 6 (IVb, 3.5 g, 9.2 mmol) was reacted with 2,3-dichloro-5,6-dicyano-p-benzoquinone (DDQ, 3.5 g, 15.4 mmol) in toluene at reflux. Purification of the crude product thus obtained gave the pure 1,4,11-triene derivative (IVd, 2.0 g, 58%). IR (ATR) $v_{max}$ 1770, 1660, 1630, 1620 cm$^{-1}$. NMR (300 mHz, CDCl$_3$) δ 1.09 (s, CH$_3$), 1.22 (s, CH$_3$), 5.6-5.8 (m, C11-H and C12-H), 6.13 (d, C4-H), 6.3 (dd, C2), 7.2 (d, C1) ppm.

EXAMPLE 8

1α,2α:15β,16β-Dimethylene-6,6-ethylene-3-oxo-17α-pregna-4,11-diene-21,17-carbolactone (IVf)

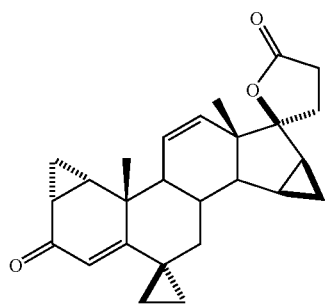

IVf

As described in Example 4, a solution of the compound of Example 7 (IVd, 1.7 g, 4.5 mmol) was reacted with trimethylsulfoxonium iodide (1.75 g, 8 mmol) and sodium hydride (60% oil suspension; 0.175 g, 7.25 mmol) in DMSO (25 mL) to give the crude product. Purification by chromatography gave the pure 1α,2α-methylene derivative (IVf, 0.6 g, 34%). IR (ATR) $v_{max}$ 1770, 1660, 1630, 1620 cm$^{-1}$. NMR (300 mHz, CDCl$_3$) δ 1.05 (s, CH$_3$), 1.35 (s, CH$_3$), 5.6-5.8 (m, C11-H and C12-H), 5.95 (s, C4-H) ppm.

EXAMPLE 9

9α-Bromo-6,6-ethylene-11β-fluoro-3-oxo-17α-pregna-4-ene-21,17-carbolactone (IXa)

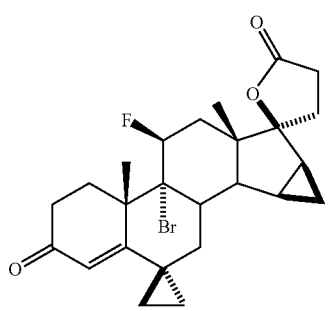

IXa

At −78° C., the compound of Example 2 (IIIb, 5.0 g, 13.2 mmol) was combined with liquid hydrogen fluoride (20 mL, ~1 M), dimethylformamide (8 mL), and N-bromosuccinimide (3.2 g, 17.98 mmol). The mixture was allowed to stand at −30° C. for 1.5 h and then introduced into ice water and ammonia solution (25%). The precipitate was filtered off, taken up in a mixture of ethyl acetate and methylene chloride, washed with water, and dried over sodium sulfate. The solvents were removed in vacuo and the residue purified by chromatography to give the pure 9α-bromo-11β-fluoro derivative (IXa, 2.0 g, 32%). IR (ATR) $v_{max}$ 1765, 1670, 1650, 1615 cm$^{-1}$. NMR (300 mHz, CDCl$_3$) δ 1.04 (s, CH$_3$), 1.66 (s, CH$_3$), 5.25 (m, C11-H), 5.8 (m, C4-H).

EXAMPLE 10

6,6-Ethylene-11β-fluoro-3-oxo-17α-pregna-4-ene-21,17-carbolactone (Vb)

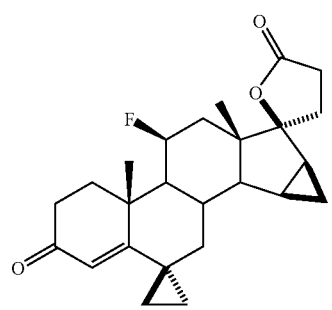

Vb

A solution of the compound of Example 9 (IXa, 3.0 g, 6.28 mmol) in tetrahydrofuran (60 mL) was treated with tributyltin hydride (7.5 mL) and α,α'-azoisobutyrodinitrile (0.05 g). The reaction mixture was stirred at room temperature for 5 h then concentrated in vacuo. The residue was purified by chromatography to give the pure 11β-fluoro derivative (Vb, 1.3 g, 52%). IR (ATR) $v_{max}$ 1765, 1670, 1650, 1615 cm$^1$. NMR (300 mHz, CDCl$_3$) δ 1.04 (s, CH$_3$), 1.66 (s, CH$_3$), 5.2 (m, C11-H), 5.8 (m, C4-H).

EXAMPLE 11

6,6-Ethylene-11β-fluoro-3-oxo-17α-pregna-1,4-diene-21,17-carbolactone (Vd)

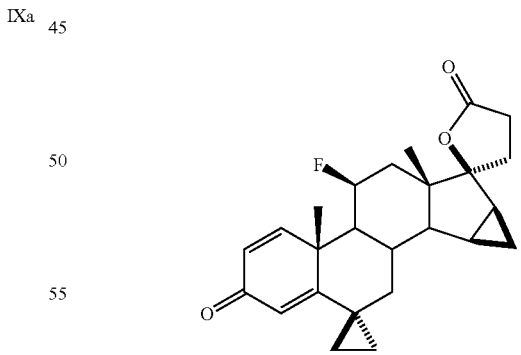

Vd

As described in Example 3, a solution of the compound of Example 10 (Vb, 3.5 g, 8.8 mmol) was reacted with 2,3-dichloro-5,6-dicyano-p-benzoquinone (DDQ, 3.5 g, 15.4 mmol) in toluene at reflux. Purification of the crude product thus obtained gave the pure 1,4-diene derivative (Vd, 1.8 g, 51%). IR (ATR) $v_{max}$ 1770, 1660, 1630, 1620 cm$^{-1}$. NMR (300 mHz, CDCl$_3$) δ 1.09 (s, CH$_3$), 1.22 (s, CH$_3$), 5.2 (m, C11-H), 6.13 (d, C4-H), 6.3 (dd, C2), 7.2 (d, C1) ppm.

EXAMPLE 12

1α,2α:15β16β-Dimethylene-6,6-ethylene-11β-fluoro-3-oxo-17α-pregna-4-ene-21,17-carbolactone (Vf)

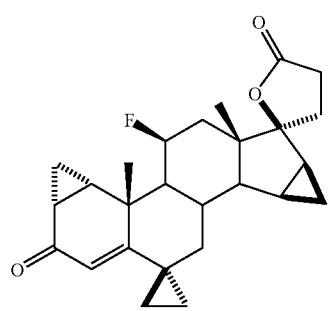

Vf

As described in Example 4, a solution of the compound of Example 11 (Vd, 1.7 g, 4.3 mmol) was reacted with trimethylsulfoxonium iodide (1.75 g, 8 mmol) and sodium hydride (60% oil suspension; 0.175 g, 7.25 mmol) in DMSO (25 mL) to give the crude product. Purification by chromatography gave the pure 1α,2α-methylene derivative (Vf, 0.6 g, 34%). IR (ATR) $v_{max}$ 1770, 1660, 1630, 1620 cm$^{-1}$. NMR (300 mHz, CDCl$_3$) δ 1.05 (s, CH$_3$), 1.35 (s, CH$_3$), 5.25 (m, C11-H), 5.95 (s, C4-H) ppm.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A progestogen compound having the structure of formula (II):

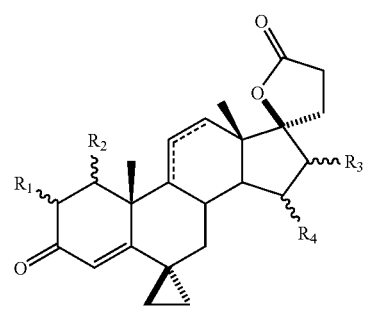

II where the dotted line in Formula II represents a double bond between carbons 9 and 11 or a double bond between carbons 11 and 12;

R$_1$ and R$_2$ are hydrogens, an additional bond between carbons 1 and 2, or a —CH$_2$—bridge between carbons 1 and 2; and R$_3$ and R$_4$ are hydrogens or a —CH$_2$—bridge between carbons 15 and 16.

2. The progestogen compound of claim 1, wherein when the progestogen compound has a double bond between carbons 9 and 11, the progestogen compound is represented by the structure of formula (III):

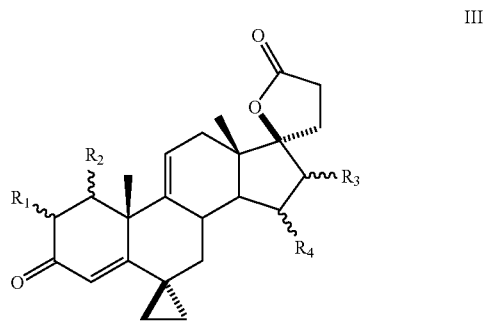

III wherein R$_1$ and R$_2$ are hydrogens, an additional bond between carbons 1 and 2, or a —CH$_2$—bridge between carbons 1 and 2; and wherein R$_3$ and R$_4$ are hydrogens or a —CH$_2$—bridge between carbons 15 and 16.

3. The progestogen compound of claim 2, wherein when the progestogen compound has a double bond between carbons 11 and 12, the progestogen compound is represented by the structure of formula (IV):

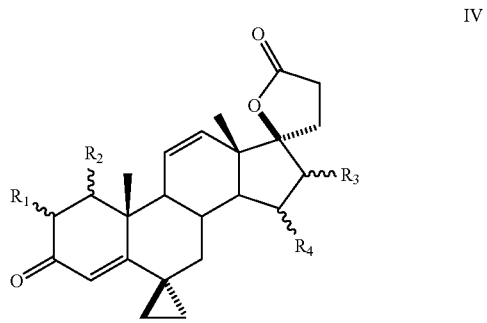

IV wherein $R_1$ and $R_2$ are hydrogens, an additional bond between carbons 1 and 2, or a —$CH_2$—bridge between carbons 1 and 2; and wherein $R_3$ and $R_4$ are hydrogens or a —$CH_2$—bridge between carbons 15 and 16.

4. A method of producing a contraceptive state in a subject comprising administering to a subject in need of an oral dosage form comprising an effective amount of a progestogen compound of formula (II):

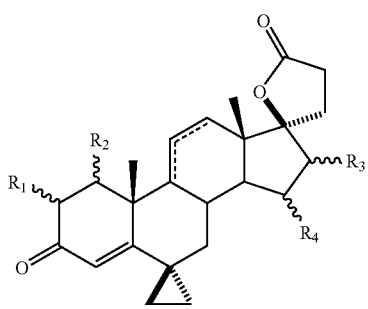

II where the dotted line in Formula II represents a double bond between carbons 9 and 11 or a double bond between carbons 11 and 12;

$R_1$ and $R_2$ are hydrogens, an additional bond between carbons 1 and 2, or a —$CH_2$— bridge between carbons 1 and 2; and $R_3$ and $R_4$ are hydrogens or a —$CH_2$— bridge between carbons 15 and 16.

5. The method of claim 4, wherein when the progestogen compound has a double bond between carbons 9 and 11, the progestogen compound is represented by the structure of formula (III):

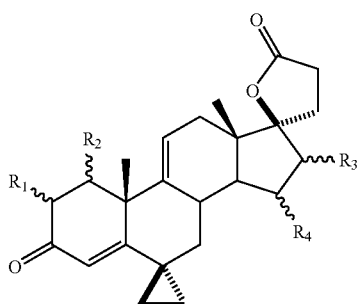

III wherein $R_1$ and $R_2$ are hydrogens, an additional bond between carbons 1 and 2, or a —$CH_2$—bridge between carbons 1 and 2; and wherein $R_3$ and $R_4$ are hydrogens or a —$CH_2$—bridge between carbons 15 and 16.

6. The method of claim 5, wherein when the progestogen compound has a double bond between carbons 11 and 12, the progestogen compound is represented by the structure of formula (IV):

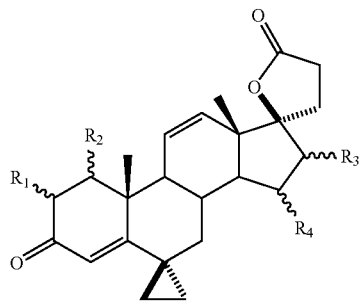

IV wherein $R_1$ and $R_2$ are hydrogens, an additional bond between carbons 1 and 2, or a —$CH_2$—bridge between carbons 1 and 2; and wherein $R_3$ and $R_4$ are hydrogens or a —$CH_2$—bridge between carbons 15 and 16.

7. The method of claim 4, wherein the oral dosage form further comprises an estrogen compound.

8. The method of claim 4, wherein the oral dosage form further comprises ethinylestradiol.

9. The method of claim 4, wherein, during a 28 day time period, the oral dosage form is administered once a day for a period of 21 consecutive days and wherein the oral dosage form is not administered for 7 consecutive days.

10. The method of claim 4, wherein, during a 28 day time period, the oral dosage form is administered once a day for a period of 21 consecutive days and wherein during 7 consecutive days of the 28 day period a second oral dosage form comprising an estrogen is administered to the subject.

11. A progestogen compound of formula (V):

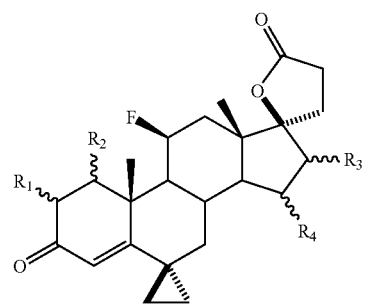

V wherein $R_1$ and $R_2$ are hydrogens, an additional bond between carbons 1 and 2, or a —$CH_2$—bridge between carbons 1 and 2; and wherein $R_3$ and $R_4$ are hydrogens or a —$CH_2$—bridge between carbons 15 and 16.

12. A method of producing a contraceptive state in a subject comprising administering to a subject in need of an oral dosage form comprising an effective amount of a progestogen compound of formula (V):

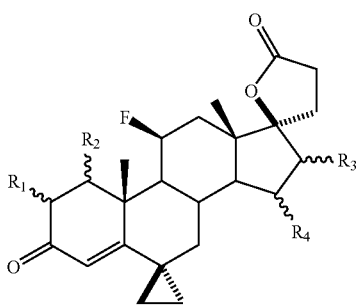

V wherein $R_1$ and $R_2$ are hydrogens, an additional bond between carbons 1 and 2, or a —CH$_2$—bridge between carbons 1 and 2; and wherein $R_3$ and $R_4$ are hydrogens or a —CH$_2$—bridge between carbons 15 and 16.

13. The method of claim 12, wherein the oral dosage form further comprises an estrogen compound.

14. The method of claim 12, wherein the oral dosage form further comprises ethinylestradiol.

15. The method of claim 12, wherein, during a 28 day time period, the oral dosage form is administered once a day for a period of 21 consecutive days and wherein the oral dosage form is not administered for 7 consecutive days.

16. The method of claim 12, wherein, during a 28 day time period, the oral dosage form is administered once a day for a period of 21 consecutive days and wherein during 7 consecutive days of the 28 day period a second oral dosage form comprising an estrogen is administered to the subject.

* * * * *